United States Patent
Kastler et al.

(10) Patent No.: US 8,598,304 B2
(45) Date of Patent: Dec. 3, 2013

(54) POLY(5,5'BIS(THIOPHEN-2-YL)-BENZO[2,1-B;3,4-B']DITHIOPHENE) AND ITS USE AS HIGH PERFORMANCE SOLUTION PROCESSABLE SEMICONDUCTING POLYMER

(75) Inventors: Marcel Kastler, Mannheim (DE); Silke Koehler, Mannheim (DE); Klaus Muellen, Cologne (DE); Miaoyin Liu, Mainz (DE); Dirk Beckmann, Harxheim (DE); Ralph Rieger, Darmstadt (DE)

(73) Assignees: BASF SE, Ludwigshafen (DE); Max-Planck-Gesellschaft zur Förderung der Wissenschaften e.V., München (DE)

( * ) Notice: Subject to any disclaimer, the term of this patent is extended or adjusted under 35 U.S.C. 154(b) by 227 days.

(21) Appl. No.: 13/002,392

(22) PCT Filed: Jun. 25, 2009

(86) PCT No.: PCT/EP2009/057984
§ 371 (c)(1),
(2), (4) Date: Mar. 18, 2011

(87) PCT Pub. No.: WO2010/000669
PCT Pub. Date: Jan. 7, 2010

(65) Prior Publication Data
US 2011/0168264 A1    Jul. 14, 2011

(30) Foreign Application Priority Data

Jul. 2, 2008 (EP) .................................. 08159524
Feb. 20, 2009 (EP) .................................. 09153369

(51) Int. Cl.
*C08G 75/00* (2006.01)

(52) U.S. Cl.
USPC .......................................... 528/377; 528/380

(58) Field of Classification Search
USPC .................................................. 528/377, 380
See application file for complete search history.

(56) References Cited

U.S. PATENT DOCUMENTS

| 5,198,153 A | 3/1993 | Angelopoulos et al. |
| 2005/0082525 A1 | 4/2005 | Heeney et al. |
| 2009/0065770 A1 | 3/2009 | Miura et al. |

FOREIGN PATENT DOCUMENTS

| EP | 0 528 662 | 2/1993 |
| EP | 1 916 250 | 4/2008 |
| WO | 96 21659 | 7/1996 |
| WO | 2006 094645 | 9/2006 |
| WO | 2006 131185 | 12/2006 |
| WO | 2007 105386 | 9/2007 |
| WO | 2009 016107 | 2/2009 |

OTHER PUBLICATIONS

U.S. Appl. No. 13/376,296, filed Dec. 5, 2012, Mishra, et al.
U.S. Appl. No. 13/378,069, filed Dec. 14, 2011, Kastler, et al.
U.S. Appl. No. 13/266,935, filed Oct. 28, 2011, Karpov, et al.
U.S. Appl. No. 13/056,987, filed Feb. 1, 2011, Kastler, et al.
Yoshida, S. et al., "Novel Electron Acceptors Bearing a Heteroquinonoid System. 4.7 Syntheses, Properties and Charge-Transfer Complexes of 2,7-Bis (dicyanomethylene)-2,7-Dihydrobenzo[2,1-b:3,4-b]dithiophene, 2,7-Bis(Dicyanomethylene)-2,7-Dihydrobenzo[1,2-b:4,3-b:4,3-bldithiophene, and 2,6-Bis(dicyanomethylene)-2,6-dihydrobenzo [1,2-b:4,5-bldithiophene", J. Org. Chem., vol. 59, No. 11, pp. 3077-3081, XP002543847 (1994).
Gallazzi, M. C. et al., "Polythiophenes With Unusual Electrical and Optical Properties Based on Donor Acceptor Alternance Strategy", Macromol. Chem. Phys., vol. 202, No. 10, pp. 2074-2085, (2001).
Van Pham, C. et al. "A Convenient Synthesis of 3-Alkylthiophenes", Synthetic Communications, vol. 16, No. 6, pp. 689-696, ISSN: 0039-7911, (1986).
Wan, J. H. et al., "JOC Additions and Corrections", J Org. Chem., vol. 71, p. 7124, (Aug. 25, 2006).
Mueller, D. et al., "Novel Cross-Linkable Hole-Transport Monomer for Use in Organic Light Emitting Diodes", Synthetic Metals, vol. 111-112, pp. 31-34, (2000).
Sanchez, C. et al., "Photoluminescence Stability of a Cyanoterphenyl Chromophore in Liquid Crystalline Polymeric Systems", Journal of Applied Physics, vol. 88, No. 12, pp. 7124-7128 (Dec. 15, 2000).

Yoon, M-H. et al., "α-π Molecular Dielectric Multilayers for Low-Voltage Organic Thin-Film Transistors", PNAS, vol. 102, No. 13, pp. 4678-4682, (Mar. 29, 2005).
International Search Report Oct. 20, 2009 in PCT/EP09/057984 filed Jun. 25, 2009.
U.S. Appl. No. 13/002,208, filed Dec. 30, 2010, Kastler, et al.
U.S. Appl. No. 13/002,425, filed Jan. 3, 2011, Kastler, et al.
U.S. Appl. No. 13/140,595, filed Jun. 17, 2011, Mishra, et al.
U.S. Appl. No. 13/128,961, filed May 12, 2011, Quinn, et al.

*Primary Examiner* — Shane Fang
(74) *Attorney, Agent, or Firm* — Oblon, Spivak, McClelland, Maier & Neustadt, L.L.P.

(57) ABSTRACT

Poly(5,5'-bis(thiophen-2-yl)-benzo[2,1-b;3,4-b'] dithiophene) comprising as repeating units the group of the formula (I) wherein R is independently selected from a) a $C_{1-20}$ alkyl group, b) a $C_{2-20}$ alkenyl group, c) a $C_{2-20}$ alkynyl group, d) a $C_{1-20}$ alkoxy group, e) a —Y—$C_{3-10}$ cycloalkyl group, f) a —Y—$C_{6-14}$ aryl group, g) a —Y-3-12 membered cycloheteroalkyl group, or h) a —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 $R^1$ groups, $R^1$ is independently selected from a) a $S(O)_m$—$C_{1-20}$ alkyl group, b) a $S(O)_m$—$OC_{1-20}$ alkyl group, c) a $S(O)_m$—$OC_{6-14}$ aryl group, d) a $C(O)$—$OC_{1-20}$ alkyl group, e) a $C(O)$—$OC_{6-14}$ aryl group, f) a $C_{1-20}$ alkyl group, g) a $C_{2-20}$ alkenyl group, h) a $C_{2-20}$ alkynyl group, i) a $C_{1-20}$ alkoxy group, j) a $C_{3-10}$ cycloalkyl group, k) a $C_{6-14}$ aryl group, l) a 3-12 membered cycloheteroalkyl group, or m) a 5-14 membered heteroaryl group, Y is independently selected from a divalent $C_{1-6}$ alkyl group, or a covalent bond; and m is independently selected from 0, 1, or 2, and having a number average molecular weight $M_n$ in the range of from 5,000 to 200,000 g/mol.

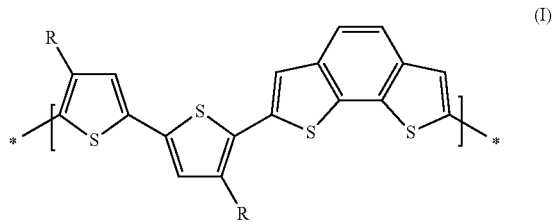

(I)

20 Claims, 4 Drawing Sheets

POLY(5,5'BIS(THIOPHEN-2-YL)-BENZO[2,1-B;3,4-B']DITHIOPHENE) AND ITS USE AS HIGH PERFORMANCE SOLUTION PROCESSABLE SEMICONDUCTING POLYMER

The present invention relates to poly(5,5'-bis(thiophen-2-yl)-benzo[2,1-b;3,4-b']dithiophene) and its use as high performance solution processable semiconducting polymer.

The formidable building block for the development of (micro)electronics during the second one-half of the 20$^{th}$ century is the field-effect transistor (FET) based on inorganic electrodes, insulators, and semiconductors. These materials have proven to be reliable, highly efficient, and with performance that increases periodically according to the well-known Moore's law. Rather than competing with conventional silicon technologies, an organic FET (OFET) based on molecular and polymeric materials may find large scale applications in low-performance memory elements as well as integrated optoelectronic devices, such as pixel drive and switching elements in active-matrix organic light-emitting diode displays, RFID tags, smart-ID tags, and sensors.

As a result of the development of several conductive or semiconductive organic polymers, the application of those as active layer, thus the semiconductor, in organic thin-film transistors (OTFTs) has gained increasing attention.

The use of organic semiconductors in OTFTs has some advantages over the inorganic semiconductors used to date. They can be processed in any form, from the fiber to the film, exhibit a high mechanical flexibility, can be produced at low cost and have a low weight. The significant advantage is, however, the possibility of producing the entire semiconductor component by deposition of the layers from solution on a polymer substrate at atmospheric pressure, for example by printing techniques, such that inexpensively producible FETs are obtained.

The performance of the electronic devices depends essentially on the mobility of the charge carriers in the semiconductor material and the ratio between the current in the on-state and the off-state (on/off ratio). An ideal semiconductor therefore has a minimum conductivity in the switched-off state and a maximum charge carrier mobility in the switched-on state (mobility above $10^{-3}$ cm$^2$V$^{-1}$s$^{-1}$ on/off ratio above $10^2$). In addition, the semiconductor material has to be relatively stable to oxidation, i.e. has to have a sufficiently high ionization potential, since its oxidative degradation reduces the performance of the component.

EP 1510535 A1 describes polythieno(2,3-b)thiophenes which have a mobility of $3 \cdot 10^{-3}$ or $1.7 \cdot 10^{-2}$ cm$^2$V$^{-1}$s$^{-1}$ and on/off ratios of about $10^6$. WO2006/094645 A1 describes polymers which have one or more selenophene-2,5-diyl and one or more thiophene-2,5-diyl groups, while WO 2006/131185 discloses polythieno(3,4-d)thiazoles, and US 2005/0082525 A1 discloses benzo(1,2-b,4,5-b')dithiophenes.

WO2007/105386 discloses homo- and copolymers of substituted benzo[2,1-b;3,4-b']dithiophene having the following repeating units:

and having weight average molecular weights of up to $10^5$ g/mol. Both reported materials show charge carrier mobilities in the range of $10^{-5}$ to $10^{-3}$ cm$^2$/Vs.

Furthermore a copolymer with bisthiophene was reported which had only a weight average molecular weight of 4100 g/mol. This material showed only very poor performance in a field effect transistor (mobility: $1.6 \times 10^{-5}$, on/off ratio: 100).

It is an object of the present invention to provide novel compounds for use as organic semiconductor materials, which are easy to synthesize, have high mobilities, a good oxidation stability, and can be processed readily.

This object is achieved by a poly(5,5'-bis(thiophen-2-yl)-benzo[2,1-b;3,4-b']dithiophene) comprising as repeating units the group of the formula (I)

wherein
R is independently selected from a) a C$_{1-20}$ alkyl group, b) a C$_{2-20}$ alkenyl group, c) a C$_{2-20}$ alkynyl group, d) a C$_{1-20}$ alkoxy group, e) a —Y—C$_{3-10}$ cycloalkyl group, f) a —Y—C$_{6-14}$ aryl group, g) a —Y-3-12 membered cycloheteroalkyl group, or h) a —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group is optionally substituted with 1-4 R$^1$ groups,
R$^1$ is independently selected from a) a S(O)$_m$—C$_{1-20}$ alkyl group, b) a S(O)$_m$—OC$_{1-20}$ alkyl group, c) a S(O)$_m$—OC$_{6-14}$ aryl group, d) a C(O)—OC$_{1-20}$ alkyl group, e) a C(O)—OC$_{6-14}$ aryl group, f) a C$_{1-20}$ alkyl group, g) a C$_{2-20}$ alkenyl group, h) a C$_{2-20}$ alkynyl group, i) a C$_{1-20}$ alkoxy group, j) a C$_{3-10}$ cycloalkyl group, k) a C$_{6-14}$ aryl group, l) a 3-12 membered cycloheteroalkyl group, or m) a 5-14 membered heteroaryl group, Y is independently selected from a divalent $C_{1-6}$ alkyl group, or a covalent bond; and
m is independently selected from 0, 1, or 2,
and having a number average molecular weight $M_n$ in the range of from 5,000 to 200,000 g/mol.

Preferred poly(5,5'-bis(thiophen-2-yl)-benzo[2,1-b;3,4-b']dithiophenes) are those comprising repeating units of formula (I) in which
R is independently selected from a) a $C_{1-20}$ alkyl group, d) a $C_{1-20}$ alkoxy group, f) a —Y—$C_{6-14}$ aryl group, as defined above,
wherein each of the $C_{1-20}$ alkyl groups and the $C_{6-14}$ aryl groups is optionally substituted with 1-4 $R^1$ groups, and
$R^1$ is independently selected from d) —C(O)—O$C_{1-20}$ alkyl, e) —C(O)—O$C_{6-14}$ aryl, f) a $C_{1-20}$ alkyl, i) $C_{1-20}$ alkoxy, k) $C_{6-14}$ aryl groups.

More preferred repeating units are those of the formula (I) in which
R is independently selected from a) a $C_{1-20}$ alkyl group, d) a $C_{1-20}$ alkoxy group, as defined above,
wherein each of the $C_{1-20}$ alkyl groups or the $C_{1-20}$ alkoxy groups is optionally substituted with 1-4 $R^1$ groups, and
$R^1$ is independently selected from f) a $C_{1-20}$ alkyl group, i) a $C_{1-20}$ alkoxy group, Particularly preferred repeating units are those of the formula (I)
in which
R is independently selected from a) a $C_{1-20}$ alkyl group, as defined above, and
wherein each of the $C_{1-20}$ alkyl groups is optionally substituted with 1-4 $R^1$ groups, and
$R^1$ is independently selected from f) a $C_{1-20}$ alkyl group.

Particularly preferred substituents R are $C_{6-20}$ alkyl groups optionally substituted with 1-4 $R^1$ groups, wherein $R^1$ is H or a $C_1$-$C_6$ alkyl group.

The advantage of the poly(5,5'-bis(thiophen-2-yl)-benzo[2,1-b;3,4-b']dithiophene) of the present invention is a significantly increased charge carrier mobility in a field effect transistor.

The number average molecular weight $M_n$ is preferably in the range of from 10.000 to 100.000 g/mol.

"Alkenyl" refers to a straight-chain or branched alkyl group having one or more carbon-carbon double bonds. Examples are ethenyl, propenyl, butenyl, pentenyl, hexenyl, butadienyl, pentadienyl and hexadienyl groups. The one or more carbon-carbon double bonds can be internal (such as in 2-butene) or terminal (such as in 1-butene). In various embodiments, an alkenyl group can have 2 to 20 carbon atoms. In some embodiments, alkenyl groups can be substituted as disclosed herein. An alkenyl group is generally not substituted with another alkenyl group, an alkyl group, or an alkynyl group.

"Alkynyl" refers to a straight-chain or branched alkyl group having one or more triple carbon-carbon bonds. Examples include ethynyl, propynyl, butynyl, pentynyl. The one or more triple carbon-carbon bonds can be internal (such as in 2-butyne) or terminal (such as in 1-butyne). In various embodiments, an alkynyl group can have 2 to 20 carbon atoms. In some embodiments, alkynyl groups can be substituted as disclosed herein. An alkynyl group is generally not substituted with another alkynyl group, an alkyl group, or an alkenyl group.

"Cycloalkyl" refers to a non-aromatic carbocyclic group including cyclized alkyl, alkenyl, and alkynyl groups. A preferred cycloalkyl group can have 3 to 10 carbon atoms. A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. Cycloalkyl groups can be substituted as disclosed herein.

"Heteroatom" refers to an atom of any element other than carbon or hydrogen and includes, for example, nitrogen, oxygen, silicon, sulfur, phosphorus, and selenium.

"Cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 12 ring atoms. One or more N, P, S, or Se atoms (e.g., N or S) in a cycloheteroalkyl ring may be oxidized (e.g., morpholine N-oxide, thiomorpholine S-oxide, thiomorpholine S,S-dioxide). Nitrogen or phosphorus atoms of cycloheteroalkyl groups can bear a substituent, in particular an alkyl group. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Preferred cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl. Cycloheteroalkyl groups can be substituted or unsubstituted.

"Aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 14 carbon atoms in its ring system, which can include multiple fused rings. Preferred aryl groups having only aromatic carbocyclic ring(s) include phenyl, 1-naphthyl (bicyclic), 2-naphthyl (bicyclic), anthracenyl (tricyclic), phenanthrenyl (tricyclic). Preferred polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Further preferred aryl groups include benzodioxanyl, benzodioxolyl, chromanyl, indolinyl groups, and the like. In some embodiments, aryl groups can be substituted as disclosed herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted or unsubstituted.

"Heteroaryl" refers to an aromatic monocyclic or polycyclic ring system containing at least one ring heteroatom. The heteroatom is preferably selected from oxygen (O), nitrogen (N), sulfur (S), silicon (Si), and selenium (Se) or a polycyclic ring system without being restricted thereto. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group can have from 5 to 14 ring atoms and contain 1-5 ring heteroatoms. Particular examples of heteroaryl groups include, for example, the 5- or 6-membered monocyclic and 5-6 bicyclic ring systems shown below:

where T is O, S, NH, N-alkyl, N-aryl, N-(arylalkyl) (e.g., N-benzyl), $SiH_2$, SiH-(alkyl), $Si(alkyl)_2$, SiH-(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as disclosed herein.

R is particularly preferred linear or branched $C_6$-$C_{20}$ alkyl, e.g. n-hexyl, n-heptyl, n-octyl, n-nonyl, n-decyl, n-undecyl, n-dodecyl, n-tridecyl, n-tetradecyl, n-pentadecyl, n-hexadecy, n-heptadecyl, n-octadecy, n-nonadecyl, n-isosyl, 1-methylpentyl, 1-methylhexyl, 2-methylpentyl, 2-ethylhexyl, and 2,7-dimethyloctyl. Particularly preferred are 2,6-dimethyloctyl, 1-ethylhexyl, 1-methylhexyl, 2-ethylpentyl, 2-methylhexyl, n-decyl, n-dodecyl, n-tetradecyl, and 2-ethylhexyl, most preferred is n-dodecyl.

"Mobility" or "mobility" refers to a measure of the velocity with which charge carriers induced by an external stimulus such as an electric field, for example, holes (or units of positive charge) in the case of a p-type semiconducting material and electrons in the case of an n-type semiconducting material, move through the material under the influence of an electric field.

The present invention further provides for the use of the copolymers according to the present invention as semiconductors or charge transport materials, especially in optical, electrooptical or electronic components, as thin-film transistors, especially in flat visual display units, or for radiofrequency identification tags (RFID tags) or in semiconductor components for organic light-emitting diodes (OLEDs), such as electroluminescent displays or backlighting for liquid-crystalline displays, for photovoltaic components or in sensors, as electrode material in batteries, as optical waveguides, for electrophotography applications such as electrophotographic recording.

The present invention further provides optical, electrooptical or electronic components comprising the polymer according to the present invention. Such components may be, for example, FETs, integrated circuits (ICs), TFTs, OLEDs or alignment layers.

The polymers according to the present invention are suitable particularly as semiconductors, since they have the mobilities required for this purpose.

The polymers may be end-capped by several groups as known from the prior art. Preferred end groups are H, substituted or unsubstituted phenyl or substituted or unsubstituted thiophene, without being restricted thereto.

The poly(5,5'-bis(thiophen-2-yl)-benzo[2,1-b;3,4-b']dithiophene) according to the present invention can be prepared by methods which are already known. A preferred synthesis route is described hereinafter.

In this scheme, R is $C_6$-$C_{20}$ alkyl.

The preparation of [2,2']bithiophenyl-3,3'-dicarbaldehyde from thiophene-3-carbaldehyde is described in M. C. Gallazzi, F. Toscano, D. Paganuzzi, C. Bertarelli, A. Farina, G. Zotti, Macromol. Chem. Phys. 2001, 202, 2074.

The preparation of benzo[2,1-b;3,4-b']dithiophene from 2,2']bithiophenyl-3,3'-dicarbaldehyde is described in S. Yoshida, M. Fujii, Y. Aso, T. Otsubo, F. Ogura, J. Org. Chem. 1994, 59, 3077.

5,5'-Bis(trimethylstannyl)benzo-2,2'-dithiophene can be prepared by adding t-butyl lithium to benzo[2,1-b;3,4-b']dithiophene in anhydrous THF, upon which a precipitate is formed. To the suspension, trimethyltin chloride is added as solid.

The preparation of 3-alkylthiophene form 3-bromothiophene is described in C. Van Pham, H. B. Mark, H. Zimmer, Synth. Comm. 1986, 16, 689.

The preparation of 4,4'-dialkyl-5,5'-dibromo-2,2'-dithiophene from 3-alkylthiophene via 4,4'-dialkyldithiophene is described in J. H. Wan, J. C. Feng, G. A. Wen, W. Wei, Q. L. Fan, C. M. Wang, H. Y. Wang, R. Zhu, X. D. Yuan, C. H. Huang, W. Huang, J. Org. Chem. 2006, 71, 7124.

Poly(5,5'-bis(3-dodecylthiophene-2-yl)-benzo[2,1-b;3,4-b']dithiophene) is prepared form 5,5'-bis(trimethylstannyl) benzo[2,1-b;3,4-b']dithiophene and 4,4'-dialkyl-5,5'-dibromo-2,2'-dithiophene in the presence of tri-o-tolylphosphine and $Pd_2(dba)_3$ (dba=dibenzylidene acetone).

The copolymers can be synthesized via a cross-coupling polymerisation reaction, such as Stille or Suzuki reaction, in which an aryl dihalide is reacted with a organotin compound or a boronic diester/acid in the presence of a base and a small amount of metal catalyst. Typically the reaction is carried out in a solvent or mixture of solvents with a reaction temperature between 20° C. and 150° C.

Essential for the synthesis of high molecular weight polymer is the high purity and therefore an appropriate purification method of the utilized monomers. The purity of the monomers (i.e. the 5,5'-dihalo-2,2'-dithiophene and the 5,5'-bis(trialkyl)benzothiophene) is in general >99%. A high purity of the 5,5'-bis(trimethylstannyl)benzo-2,2'-dithiophene can be obtained by repeated recrystallisation (preferably at least three time) at low temperature from acetonitrile. This purification yields the monomer in the form of colorless needles.

The 4,4'-alkyl-5,5'-dibromo-2,2'-dithiophene monomer can be obtained with very high purity by purification by column chromatography (n-hexane, Silica) followed by repeated recrystallisation from ethylacetate.

The use of monomers with a significantly lower purity than 99% leads to a polymer of much lower molecular weight.

The second important factor is the adjustment of the monomer ratio. An equimolar mixture yields the desired molecular weight.

The molecular weight can be reproducibly obtained by adjusting the concentration of the 1:1 monomer mixture. In order to obtain a high number average molecular weight of 15-20 kg/mol, the optimum, total concentration of the monomers is in the range of from 10 to 20 wt %.

The invention comprises both the oxidized and the reduced forms of the polymers according to the present invention. Either a deficiency or an excess of electrons leads to the formation of a delocalized ion which has a high conductivity. This can be done by doping with customary dopants. Dopants and doping processes are common knowledge and are known, for example, from EP-A 0 528 662, U.S. Pat. No. 5,198,153 or WO 96/21659. Suitable doping processes comprise, for example, doping with a doping gas, electrochemical doping in a solution comprising the dopant, by thermal diffusion and by ion implantation of the dopant into the semiconductor material.

In the case of use of electrons as charge carriers, preference is given to using halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), inorganic acids (e.g. HF, HCl, $HNO_3$, $H_2SO_4$, $HClO_4$, $FSO_3H$ and $ClSO_3H$), organic acids or amino acids, transition metal compounds (e.g. $FeCl_3$, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (where Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF6^-$, $FeCl_4^-$, $Fe(CN)_6^{3-}$, and anions of different sulfonic acids such as aryl-$SO_3^-$). In the case of use of holes as charge carriers, as dopants, for example, are cations (e.g. $H^+$, $Li^+$, $Na^+$, $K^+$, $Rb^+$ and $Cs^+$), alkali metals (e.g. Li, Na, K, Rb, and Cs), alkaline earth metals (e.g. Ca, Sr and Ba), $O_2$, $XeOF_4$, $(NO_2^+)$ $SbF_6^-)$, $(NO_2^+)$ $(SbCl_6^-)$, $(NO_2^+)$ $(BF_4^-)$, $AgClO_4$, $H_2IrCl_6$, $La(NO_3)_3$, $FSO_2OOSO_2F$, Eu, acetylcholine, $R_4N^+$, $R_4P^+$, $R_6As^+$ and $R_3S^+$, where R is an alkyl group.

The conductive form of the copolymers according to the present invention can be used as an organic conductor, for example charge injection layers and ITO planarizing layers in organic light-emitting diodes (OLEDs), flat screens and touch screens, antistatic films, printed circuits and capacitors, without being restricted thereto.

The copolymers according to the present invention can be used to produce optical, electronic and semiconductor materials, especially as charge transport materials in field-effect transistors (FETs), for example as components of integrated circuits (ICs), ID tags or TFTs. Alternatively, they can be used in organic light-emitting diodes (OLEDs) in electroluminescent displays or as backlighting, for example liquid-crystal displays (LCDs), in photovoltaic applications or for sensors, for electrophotographic recording and other semiconductor applications.

Since the copolymers according to the present invention have good solubility, they can be applied to the substrates as solutions. Layers can therefore be applied with inexpensive processes, for example spin-coating.

Suitable solvents or solvent mixtures comprise, for example, alkanes, aromatics, especially their fluorinated derivatives.

FETs and other components comprising semiconductor materials, for example diodes, can be used advantageously in ID tags or security labels in order to indicate authenticity and to prevent forgeries of valuable items such as banknotes, credit cards, identity documents such as ID cards or driving licenses or other documents with pecuniary advantage such as rubber stamps, postage stamps or tickets, etc.

Alternatively, the polymers according to the present invention can be used in organic light-emitting diodes (OLEDs), for example in displays or as backlighting for liquid-crystal displays (LCDs). Typically, OLEDs have a multilayer structure. A light-emitting layer is generally embedded between one or more electron- and/or hole-transporting layers. When an electrical voltage is applied, the electrons or holes can migrate in the direction of the emitting layer, where their recombination to the excitation and subsequent luminescence of the luminophoric compounds in the emitting layer. The polymers, materials and layers may, according to their electrical and optical properties, find use in one or more of the transport layers and/or emitting layers. When the compounds, materials or layers are electroluminescent or have electroluminescent groups or compounds, they are particularly suitable for the emitting layer.

Like the processing of suitable polymers for use in OLEDs, the selection is common knowledge and is described, for example, in Synthetic Materials, 111-112 (2000), 31-34 or J. Appl. Phys., 88 (2000) 7124-7128.

Various deposition techniques, including deposition from various solution processing techniques, have been used with organic semiconductors. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. Micro dispensing is another noncontact method of printing. However, contact printing techniques have the advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like. Other solution processing techniques include, for example, spin coating, drop-casting, zone casting, dip coating, blade coating, or spraying.

Various articles of manufacture including electronic devices, optical devices, and optoelectronic devices, such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds disclosed herein also are within the scope of the present teachings as are methods of making the same.

The present teachings, therefore, further provide methods of preparing a semiconductor material. The methods can include preparing a composition that includes one or more compounds disclosed herein dissolved or dispersed in a liquid medium such as solvent or a mixture of solvents, depositing the composition on a substrate to provide a semiconductor material precursor, and processing (e.g. heating) the semiconductor precursor to provide a semiconductor material (e.g. a thin film semiconductor) that includes a compound disclosed herein. In various embodiments, the liquid medium is an organic solvent, an inorganic solvent such as water, or combinations thereof. In some embodiments, the composition can further include one or more additives independently selected from detergents, dispersants, binding agents, compatiblizing agents, curing agents, initiators, humectants, antifoaming agents, wetting agents, pH modifiers, biocides, and bacteriostats. For example, surfactants and/or other polymers (e.g., polystyrene, polyethylene, poly-alpha-methylstyrene, polyisobutene, polypropylene, polymethylmethacrylate, and the like can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone-casting, dip coating, blade coating, or spraying.

The present teachings further provide articles of manufacture such as the various devices described herein that include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate) and self-assembled superlattice/self-assembled nanodielectric (SAS/SAND) materials (e.g., described in Yoon, M-H. et al., PNAS, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which materials of the present teachings are useful are photovoltaics or solar cells. Components of the present teachings can exhibit broad optical absorption and/or a very positively shifted reduction potential, making them desirable for such applications. Accordingly, the substances described herein can be used as a p-type semiconductor in a photovoltaic design, which includes an adjacent n-type semiconducting material that forms a p-n junction. The compounds can be in the form of a thin film semiconductor, which can be deposited on a substrate to form a composite. Exploitation of small molecules of the present teachings in such devices is within the knowledge of a skilled artisan.

Figure 1:
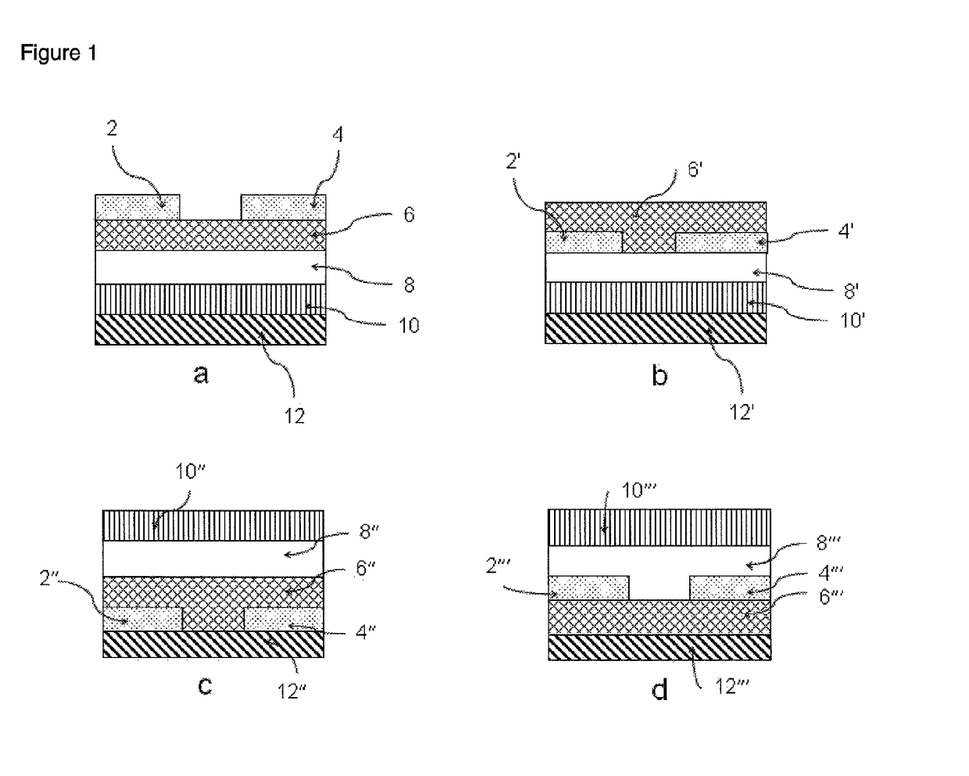
FIG. 1 illustrates the four common types of OFET structures: top-contact bottom-gate structure (a), bottom-contact bottom-gate structure (b), bottom-contact top-gate structure (c), and top-contact top-gate structure (d).

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 1 illustrates the four common types of OFET structures: top-contact bottom-gate structure (a), bottom-contact bottom-gate structure (b), bottom-contact top-gate structure (c), and top-contact top-gate structure (d). As shown in FIG. 1, an OFET can include a dielectric layer (e.g., shown as 8, 8', 8", and 8"' in FIGS. 1a, 1b, 1c, and 1d, respectively), a semiconductor layer (e.g., shown as 6, 6', 6", and 6"' in FIGS. 1a, 1b, 1c, and 1d, respectively), a gate contact (e.g., shown as 10, 10', 10", and 10"' in FIGS. 1a, 1b, 1c, and 1d, respectively), a substrate (e.g., shown as 12, 12', 12", and 12"' in FIGS. 1a, 1b, 1c, and 1d, respectively), and source and drain contacts (e.g., shown as 2, 2', 2", 2"', 4, 4', 4", and 4"' in FIGS. 1a, 1b, 1c, and 1d, respectively).

In certain embodiments, OTFT devices can be fabricated with the present compounds on doped silicon substrates, using $SiO_2$ as the dielectric, in top-contact geometries. In particular embodiments, the active semiconducting layer which incorporates at least a material of the present teachings can be deposited at room temperature or at an elevated temperature. In other embodiments, the active semiconducting layer which incorporates at least a compound of the present teachings can be applied by spin-coating or printing as described herein. For top-contact devices, metallic contacts can be patterned on top of the films using shadow masks.

All quantitative data (percentages, ppm, etc.) are based on the weight, based on the total weight of the mixture, unless stated otherwise.

All documents cited herein are incorporated in the present patent application by reference. All quantitative data (percentages, ppm, etc.) are based on the weight, based on the total weight of the mixture, unless stated otherwise.

EXAMPLES

Example 1

Preparation of 5,5'-Bis(trimethylstannyl)benzo-2,2'-dithiophene 250 mg (1.3 mmol) benzo[2,1-b;3,4-b']dithiophene are dissolved in 10 ml anhydrous THF under argon. The solution is cooled to −78° C., then 2.3 ml t-butyl lithium (3.9 mmol, 3 eq) are added upon which a white precipitated is formed. The suspension is stirred for another 2 hours at −78° C., 900 mg (4.5 mmol) trimethyltin chloride are added as solid. The solution is slowly warmed to room temperature over night. 30 ml methylene chloride are added to the solution, extracted with sodium bicarbonate, dried and the solvent is evaporated. The residue is crystallized three times from acetonitrile at 4° C. to yield colorless needles (300 mg, 44%). Mp=87° C.; MS (FD, 8 kV) m/z 516.1 g/mol—calculated: 515.9 g/mol for $C_{16}H_{22}S_2Sn_2$ $^1$H-NMR (250 MHz, $CD_2Cl_2$, RT): δ 7.74 (s, 2H), δ 7.53 (s, 2H), δ 0.45 (s, 18H); $^{13}$C-NMR (62.5 MHz, $CD_2Cl_2$, RT): δ 138.9, 138.8, 138.3, 133.3, 120.1, −8.0

Example 2

The preparation of 4,4'-dialkyl-5,5'-dibromo-2,2'-dithiophene from 3-alkylthiophene via 4,4'-dialkyldithiophene was carried out as described in J. H. Wan, J. C. Feng, G. A. Wen, W. Wei, Q. L. Fan, C. M. Wang, H. Y. Wang, R. Zhu, X. D. Yuan, C. H. Huang, W. Huang, J. Org. Chem. 2006, 71, 7124.

In order to obtain the monomer with a purity >99%, the 4,4'-dialkyl-5,5'-dibromo-2,2'-dithiophene was purified by column chromatography (n-hexane, Silica) and crystallized three times from ethylacetate to yield a crystalline product.

Example 3

Preparation of Poly(5,5'-bis(3-dodecylthiophen-2-yl)-benzo[2,1-b;3,4-b']dithiophene)

-continued 103.17 mg (0.2 mmol) 5,5'-bis(trimethylstannyl)benzo-2,2'-dithiophene and 132.14 mg (0.2 mmol) 4,4'-didodecyl-5,5'-dibromo-2,2'-dithiophene are dissolved in 2 ml anhydrous 1,2-dichlorobenzene under argon. 5 mg (16 μmol) tri-o-tolylphosphine and 4 mg (4 mmol) Pd2(dba)3 are added. The resulting mixture is heated to 140° C. for three days. The solution is diluted with 1,2-dichlorobenzene and precipitated in methanol. After filtration the polymer is reprecipitated twice in methanol and dried. 120 mg of a red solid is obtained (87%). GPC (1,2,4-trichlorobenzene, 135° C.) analysis gives $M_n$=21 000 g/mol and $M_w$=54 000 g/mol against polystyrene standard. $^1$H-NMR (500 MHz, 80° C., 1,2,4-trichlorobenzene-$d_3$) δ 7.79 (s, 2H), δ 7.59 (s, 2H), δ 7.29 (s, 2H), δ 3.09 (t, J=6.8 Hz, 4H), δ 1.96 (quin, J=6.7 Hz, 4H), δ 1.65 (quin, J=6.9 Hz, 4H), δ 1.54 (quin, J=6.7 Hz, 4H), δ 1.5-1.3 (m, 28H), δ 1.01 (t, J=6.8 Hz, 6H)

Example 4

Preparation of Poly(5,5'-bis(3-decylthiophene-2-yl)-benzo[2,1-b;3,4-b']dithiophene)

103.17 mg (0.2 mmol) 5,5'-Bis(trimethylstannyl)benzo-2,2'-dithiophene and 120.92 mg (0.2 mmol) 4,4'-didecyl-5,5'-dibromo-2,2'-dithiophene are dissolved in 2 ml anhydrous 1,2-dichlorobenzene under argon. 5 mg (16 μmol) tri-o-tolylphosphine and 4 mg (4 mmol) Pd$_2$(dba)$_3$ are added. The resulting mixture is heated to 140° C. for three days. The solution is diluted with 1,2-dichlorobenzene and precipitated in methanol. After filtration the polymer is reprecipitated twice in methanol and dried in high vacuum. 100 mg of a red solid is obtained (79%). GPC (1,2,4-trichlorobenzene, 135° C.) analysis gives $M_n$=13 kg/mol and $M_w$=29 kg/mol against polystyrene standard. $^1$H-NMR (500 MHz, 100° C., 1,2-dichlorobenzene-$d_4$) δ 7.65 (s, 2H), δ 7.46 (s, 2H), δ 7.17 (s, 2H), δ 2.93 (t, J=7.6 Hz, 4H), δ 1.79 (quin, J=7.3 Hz, 4H), δ 1.47 (quin, J=7.2 Hz, 4H), δ 1.37 (quin, J=6.5 Hz, 4H), δ 1.5-1.3 (m, 20H), δ 0.85 (t, J=6.6 Hz, 6H)

Example 5

Preparation of Poly(5,5'-bis(3-tetradecylthiophene-2-yl)-benzo[2,1-b;3,4-b']dithiophene)

103.17 mg (0.2 mmol) 5,5'-Bis(trimethylstannyl)benzo-2,2'-dithiophene and 143.36 mg (0.2 mmol) 4,4'-ditetradecyl-5,5'-dibromo-2,2'-dithiophene are reacted with 5 mg (16 μmol) tri-o-tolylphosphine and 4 mg (4 mmol) Pd$_2$(dba)$_3$ in 2 ml anhydrous 1,2-dichlorobenzene as described above.

After the same workup procedure as described above, 135 mg (91%) of a red solid are obtained. GPC (1,2,4-trichlorobenzene, 135° C.) analysis gives $M_n$=20 kg/mol and $M_w$=44 kg/mol against polystyrene standard. $^1$H-NMR (500 MHz, 100° C., 1,2-dichlorobenzene-$d_4$) δ 7.66 (s, 2H), δ 7.46 (s, 2H), δ 7.18 (s, 2H), δ 2.93 (t, J=6.9 Hz, 4H), δ 1.79 (quin, J=6.7 Hz, 4H), δ 1.48 (quin, J=6.5 Hz, 4H), δ 1.38 (quin, J=6.5 Hz, 4H), δ 1.5-1.3 (m, 36H), δ 0.85 (t, J=6.5 Hz, 6H)

Example 6

Preparation of Poly(5,5'-bis(3-hexadecylthiophen-2-yl)-benzo[2,1-b;3,4-b']dithiophene)

103.17 mg (0.2 mmol) 5,5'-Bis(trimethylstannyl)benzo-2,2'-dithiophene and 154.58 mg (0.2 mmol) 4,4'-dihexadecyl-5,5'-dibromo-2,2'-dithiophene are reacted with 5 mg (16 μmol) tri-o-tolylphosphine and 4 mg (4 mmol) Pd$_2$(dba)$_3$ in 2 ml anhydrous 1,2-dichlorobenzene as described above.

After the same workup procedure as described above, 140 mg (87%) of a red solid are obtained. GPC (1,2,4-trichlorobenzene, 135° C.) analysis gives $M_n$=16 kg/mol and $M_w$=34 kg/mol against polystyrene standard. $^1$H-NMR (500 MHz, 100° C., 1,2-dichlorobenzene-$d_4$) δ 7.66 (s, 2H), δ 7.47 (s, 2H), δ 7.17 (s, 2H), δ 2.94 (t, J=7.2 Hz, 4H), δ 1.80 (quin, J=7.1 Hz, 4H), δ 1.46 (quin, J=6.8 Hz, 4H), δ 1.38 (quin, J=6.5 Hz, 4H), δ 1.5-1.3 (m, 44H), δ 0.85 (t, J=6.5 Hz, 6H)

Example 7

FET Device Preparation and Measurement I

Organic field-effect transistors (OFETs) provide a simple device structure that allows detailed analysis of charge transport characteristics of materials via evaluation of the current-voltage response. The function of the OFET is to modulate the semiconductor conductivity between the source and drain electrodes as a function of the gate voltage. A top-contact/bottom-gate configuration device in which the source and drain were vapor-deposited on top of the semiconductor film was used in this example. OFET structure was selected to access polymer conduction capabilities but does not limit the fields of use of this material class.

Figure 2:
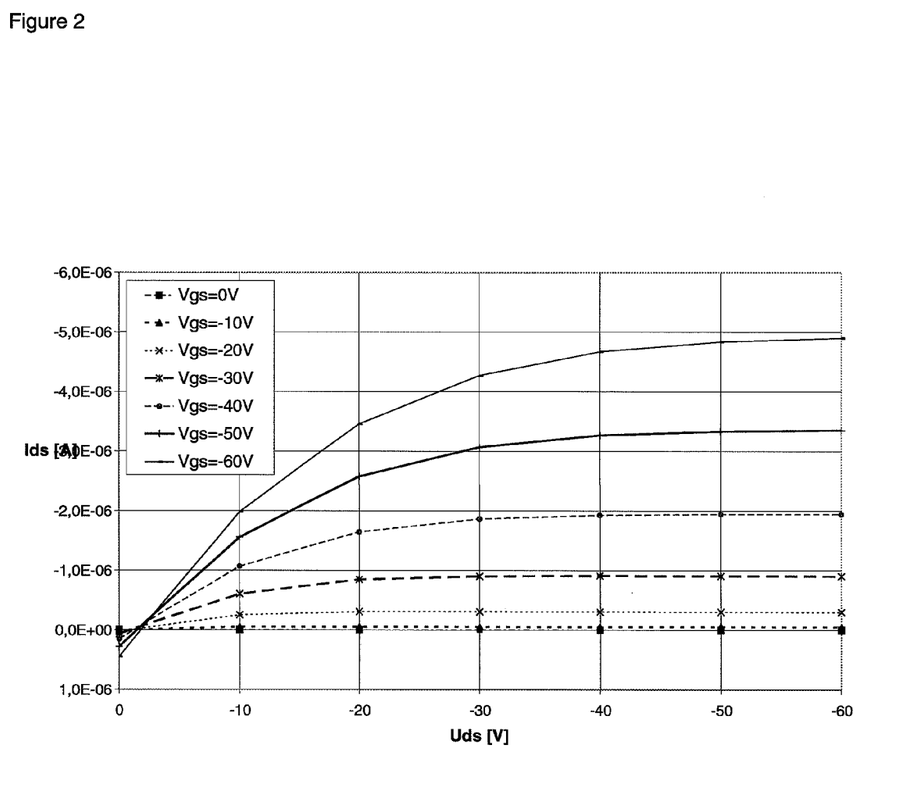
FIG. 2 shows, as relates to the devices discussed in Example 7, exemplary transfer and output plots measured in vacuum.

For the devices fabricated and studied in this example, the gate was highly doped silicon, while the dielectric was a 300-nm thick $SiO_2$ film. The semiconductor polymeric film was prepared by spin-coating a solution of the polymer prepared according to example 3 in o-dichlorobenzene (1 mg/mL) onto vapor-n-octyltrichlorosilane-treated substrates at a spin rate of 1000 rpm. Top-contact TFTs were fabricated by vapor-depositing Au ($3 \times 10^{-6}$ Torr, 0.1 Å/s, ~100 nm thick) onto the semiconductor thin films through a shadow mask to obtain devices with a channel widths of between 25-200 □m and lengths of about 1 to 5 mm. Electrical measurements were performed with a Keithley 2612 machine at ambient. Transfer plots of $I_d$ vs. $V_g$ were used to calculate the saturation mobility, threshold voltage, and current on-off ratio for all devices. To compare the electrical properties across the series, all parameters were calculated for a $V_d$ ensuring that the device was operating in the saturation regime ($V_d > V_g$). FIG. 2 shows exemplary transfer and output plots of such devices measured in vacuum. Carrier mobilities are as high as $5 \times 10^{-2}$ cm$^{-2}$/Vs and $I_{on}/I_{off} > 10^4$ at ambient conditions.

| mobility/cm$^2$/Vs | $I_{on}/I_{off}$ | threshold voltage/V |
|---|---|---|
| $4.9 \times 10^{-2}$ | $10^5$ | 8 |

Figure 3:
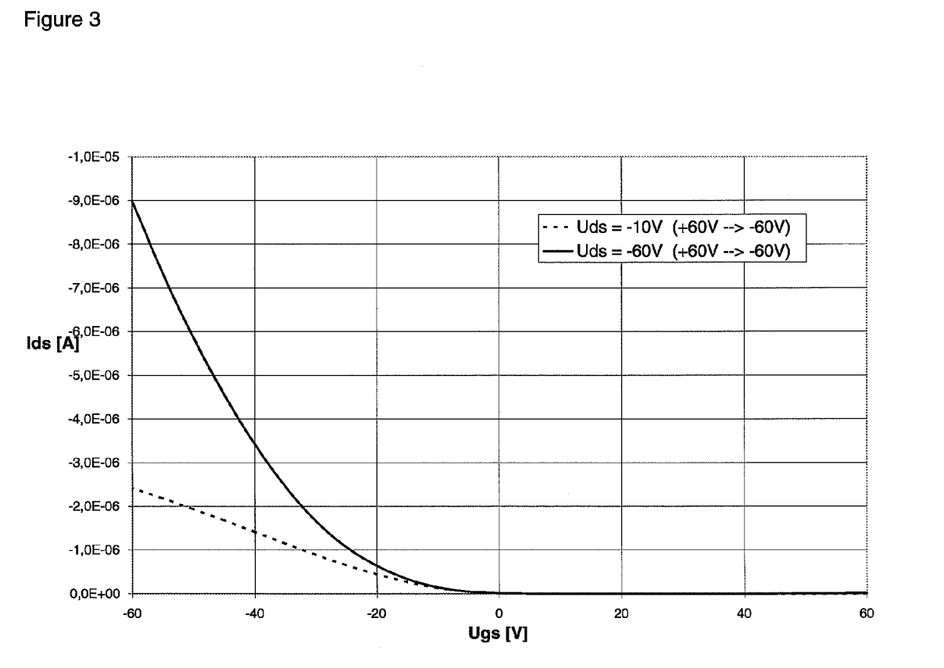
FIG. 3 shows, as relates to the devices discussed in Example 7, exemplary transfer and output plots measured at ambient conditions.

FIG. 3 shows exemplary transfer (right, Vsd=−10V, −60V) and output (left, Vsg=0, −10, −20, −30, −40, −50, −60V) plots measured at ambient conditions.

Example 8

FET Device Preparation and Measurement II

For all devices, heavily doped silicon wafers with a 200 nm thick thermally grown silicon dioxide layer were used as substrates. Hexamethyldisilazane was deposited out of the gas phase at 120° C. The semiconductor polymeric film was prepared by spin-coating (3000 rpm, 60 s) a 5 mg/ml 1,2-dichlorobenzene solution (roughly 47.5 nm thick) of the polymers prepared according to Examples 3-6. After annealing the substrate at 100° C. for 30 min and slow cooling (1° C./min), source and drain electrodes were fabricated by vapor-depositing gold (3×10-6 bar, 1 Å/s, ~100 nm thick) onto the semiconductor thin films through a shadow mask to obtain devices with channel lengths of between 25-75 μm and of widths about 0.5 to 1.5 mm (W/L=20). All preparations and electrical measurements using a Keithley 4200 semiconductor parameter analyzer were performed under nitrogen atmosphere in yellow light.

The device performance is measured at five different positions of the wafer, average results with standard deviations are summarized in table 1 below.

TABLE 1

| R | $\mu_{sat}$ in cm$^2$/Vs | $I_{on/off}$ |
|---|---|---|
| $C_{10}H_{21}$ | 0.070 ± 0.009 | $(1.7 \pm 1.0) \cdot 10^5$ |
| $C_{12}H_{25}$ | 0.106 ± 0.012 | $(1.8 \pm 1.3) \cdot 10^5$ |
| $C_{14}H_{29}$ | 0.094 ± 0.005 | $(9.2 \pm 1.2) \cdot 10^5$ |
| $C_{16}H_{33}$ | 0.066 ± 0.008 | $(3.4 \pm 3.6) \cdot 10^5$ |

Example 9

Solar Cell Device Preparation and Measurement

The patterned ITO substrates were first cleaned with acetone and isopropyl alcohol in an ultrasonic bath, followed by a cleaning treatment for 10 min with oxygen plasma. Subsequently, a conducting layer of poly(3,4-ethylenedioxythiophene)poly(styrene-sulfonate) (PEDOT:PSS) (Baytron® P von H. C. Starck) was spin-cast (5000 rpm) with thickness about 40 nm from aqueous solution. The substrates were dried at 150° C. for 10 min in air, and then moved into a glove-box for spin-casting the photoactive layer. The dichlorobenzene solution comprising of polybenzodithiophene (8 mg/mL) and [70] [6,6]-phenyl-C61-butyric acid methyl ester (PCBM) (16 mg/mL) was then spin-cast at 700 rpm on top of the PEDOT:PSS layer. A silver layer (ca. 100 nm) was subsequently evaporated through a mask onto the surface to form the cathode. Post-deposition annealing was carried out in the glove-box every two minutes in a stepwise way. The effective areas of the devices are about 6 mm$^2$ as defined by the overlap between the etched ITO and the top electrode. Accurate values of these areas were determined using a microscope for subsequent calculations. Incident light was focused on the effective area of each device through a lens. Current-wavelength curves were recorded with a Keithley 236 Source-Measure Unit. A tungsten halogen lamp was employed as a light source, supplying monochromatic light from 300 to 800 nm through a TRIAX 180 monochromator. The incident light intensity was determined using a calibrated silicon diode. The maximum intensity was 1 W/m$^2$ at ca. 600 nm. Solar light was obtained from a solar simulator (Lichttechnik, Germany) using a 575 W metal halide lamp, in combination with an optical dichroism Filter, to produce a spectral distribution close to the global radiation AM1.5G. The light intensity was adjusted to 1000 W/m$^2$.

The bulk-heterojunction solar cells based on polybenzodithiophene as donor and [70]PCBM as acceptor upon stepwise post-deposition annealing showed a power-conversion efficiency of 2.68% under AM1.5 simulated solar illumination of 1000 W/m$^2$, with short-circuit current Isc=8.53 mA/cm$^2$, open-circuit voltage Voc=0.67 V and a fill factor FF=0.46. The highest external quantum efficiency (EQE) of 27% was achieved at 420 nm (FIG. 4).

Figure 4A:
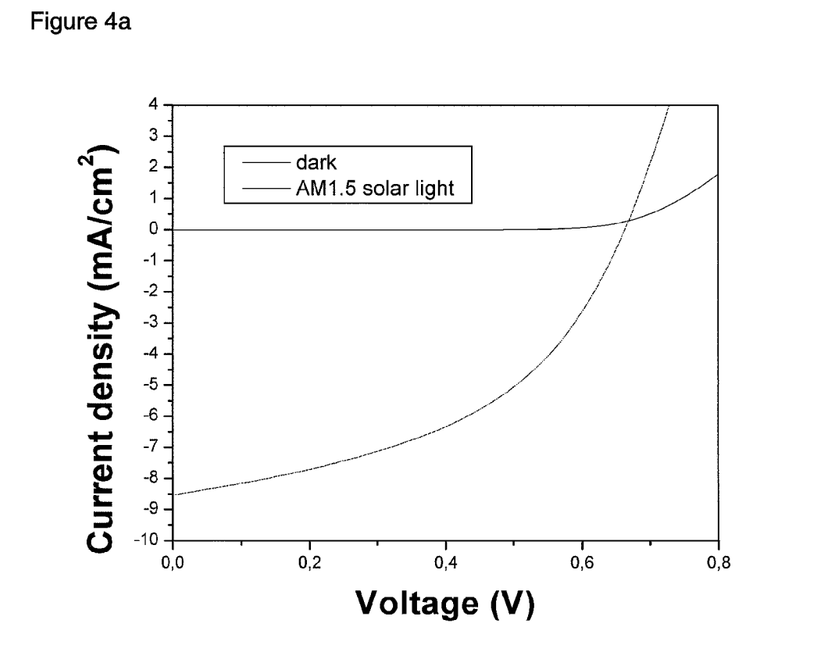
FIGS. 4a, 4b show current density-voltage curve (a) and EQE-wavelength curve (b) of photovoltaic devices of ITO/PEDOT-PSS/D:A/Ag under AM1.5 simulated solar illumination of 1000 W/m$^2$.
Figure 4B:
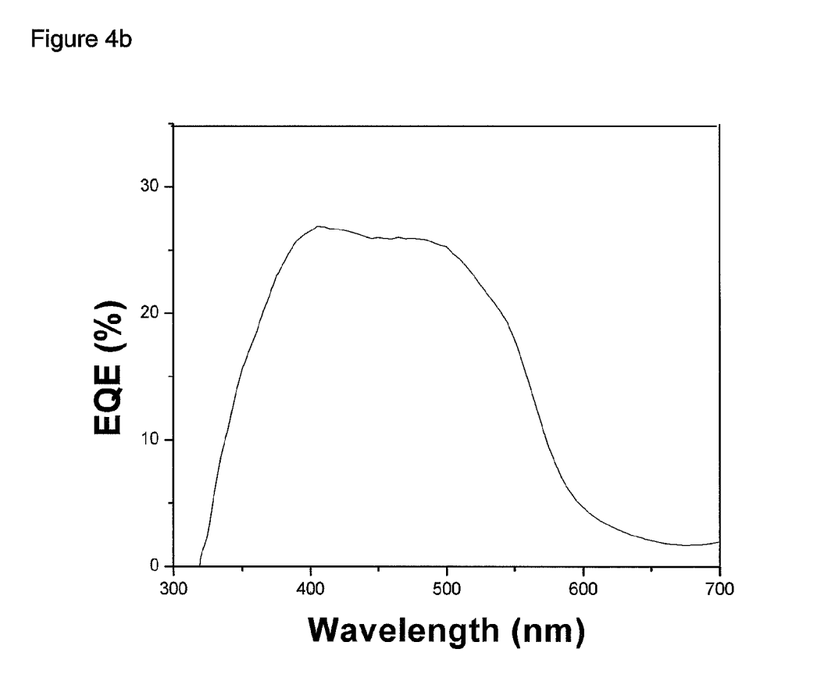

FIGS. 4a, b show Current density-voltage curve (a) and EQE-wavelength curve (b) of photovoltaic devices of ITO/PEDOT-PSS/D:A/Ag under AM1.5 simulated solar illumina-

The invention claimed is:

1. A poly(5,5'-bis(thiophen-2-yl)-benzo[2,1-b;3,4-b']dithiophene), comprising as a repeating unit at least one group of formula (I)

wherein
R is independently a) a $C_{1-20}$ alkyl group, b) a $C_{2-20}$ alkenyl group, c) a $C_{2-20}$ alkynyl group, d) a $C_{1-20}$ alkoxy group, e) a —Y—$C_{3-10}$ cycloalkyl group, f) a —Y—$C_{6-14}$ aryl group, g) a —Y-3-12 membered cycloheteroalkyl group, or h) a —Y-5-14 membered heteroaryl group,
wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 $R^1$ groups,
$R^1$ is independently a) a $S(O)_m$—$C_{1-20}$ alkyl group, b) a $S(O)_m$—$OC_{1-20}$ alkyl group, c) a $S(O)_m$—$OC_{6-14}$ aryl group, d) a $C(O)$—$OC_{1-20}$ alkyl group, e) a $C(O)$—$OC_{6-14}$ aryl group, f) a $C_{1-20}$ alkyl group, g) a $C_{2-20}$ alkenyl group, h) a $C_{2-20}$ alkynyl group, i) a $C_{1-20}$ alkoxy group, j) a $C_{3-10}$ cycloalkyl group, k) a $C_{6-14}$ aryl group, l) a 3-12 membered cycloheteroalkyl group, or m) a 5-14 membered heteroaryl group,
Y is independently a divalent $C_{1-6}$ alkyl group, or a covalent bond; and
m is independently 0, 1, or 2,
and having a number average molecular weight $M_n$ in a range of from 5,000 to 200,000 g/mol.

2. A composition, comprising the at least one poly(5,5'-bis(thiophen-2-yl)-benzo[2,1-b;3,4-b']dithiophene of claim 1 dissolved or dispersed in a liquid medium.

3. A thin film semiconductor, comprising the at least one poly(5,5'-bis(thiophen-2-yl)-benzo[2,1-b;3,4-b']dithiophene of claim 1.

4. A composite, comprising:
a substrate; and
the thin film semiconductor of claim 3 deposited on the substrate.

5. A process for preparation of a composite comprising a substrate and a thin film semiconductor
dissolving the at least one poly(5,5'-bis(thiophen-2-yl)-benzo[2,1-b;3,4-b']dithiophene of claim 1 in a liquid medium to form a solution;
depositing the solution on a substrate; and
removing solvent to form a thin film semiconductor on the substrate, thereby giving the composite comprising the substrate and the thin film.

6. The process according to claim 5, wherein the solution is deposited by spin coating, drop casting, dip coating, or printing.

7. A field effect transistor device, comprising the thin film semiconductor of claim 3.

8. A photovoltaic device, comprising the thin film semiconductor of claim 3.

9. An organic light emitting diode device, comprising the thin film semiconductor of claim 3.

10. A field effect transistor device, comprising the composition of claim 4.

11. A photo voltaic device, comprising the composite of claim 4.

12. An organic light emitting diode device, comprising the composite of claim 4.

13. The poly(5,5'-bis(thiophen-2-yl)-benzo[2,1-b;3,4-b']dithiophene) of claim 1, wherein:
R is independently a) a $C_{1-20}$ alkyl group, d) a $C_{1-20}$ alkoxy group, e) a —Y—$C_{3-10}$ cycloalkyl group, or f) a —Y—$C_{6-14}$ aryl group,
wherein each $C_{1-20}$ alkyl group and the $C_{6-14}$ aryl group is optionally substituted with 1-4 $R^1$ groups, and
$R^1$ is independently d) a $C(O)$—$OC_{1-20}$ alkyl group, e) a $C(O)$—$OC_{6-14}$ aryl group, f) a $C_{1-20}$ alkyl group, i) a $C_{1-20}$ alkoxy group, or k) a $C_{6-14}$ aryl group.

14. The poly(5,5'-bis(thiophen-2-yl)-benzo[2,1-b;3,4-b']dithiophene) of claim 1, wherein:
R is independently is independently a) a $C_{1-20}$alkyl group or d) a $C_{1-20}$ alkoxy group, wherein each $C_{1-20}$ alkyl group and the $C_{1-20}$ alkoxy group is optionally substituted with at least one 1-4 $R^1$ group,
$R^1$ is independently 0 a $C_{1-20}$ alkyl group, or i) a $C_{1-20}$ alkoxy group.

15. The poly(5,5'-bis(thiophen-2-yl)-benzo[2,1-b;3,4-b']dithiophene) of claim 1, wherein:
R is independently a $C_{1-20}$ alkyl group, optionally substituted with 1-4 $C_{1-20}$ alkyl groups.

16. The poly(5,5'-bis(thiophen-2-yl)-benzo[2,1-b;3,4-b']dithiophene) of claim 1, wherein:
R is independently a $C_{6-20}$ alkyl group, optionally substituted with 1-4 $C_{1-6}$ alkyl groups.

17. The poly(5,5'-bis(thiophen-2-yl)-benzo[2,1-b;3,4-b']dithiophene) of claim 1, wherein $M_n$ is in a range of from 10,000 to 100,000 g/mol.

18. The poly(5,5'-bis(thiophen-2-yl)-benzo[2,1-b;3,4-b']dithiophene) of claim 13, wherein $M_n$ is in a range of from 10,000 to 100,000 g/mol.

19. The poly(5,5'-bis(thiophen-2-yl)-benzo[2,1-b;3,4-b']dithiophene) of claim 14, wherein $M_n$ is in a range of from 10,000 to 100,000 g/mol.

20. The poly(5,5'-bis(thiophen-2-yl)-benzo[2,1-b;3,4-b']dithiophene) of claim 15, wherein $M_n$ is in a range of from 10,000 to 100,000 g/mol.

* * * * *